United States Patent [19]

Tsang et al.

[11] Patent Number: 4,983,590
[45] Date of Patent: Jan. 8, 1991

[54] FUNGICIDAL TRIAZOLE BIS(TRIPHENYLBORANES), DERIVATIVES THEREOF AND USE THEREOF

[75] Inventors: Tsze H. Tsang, El Cerrito; Jon L. Strutzel, Fresno, both of Calif.

[73] Assignee: Chevron Research and Technology Company, San Francisco, Calif.

[21] Appl. No.: 494,017

[22] Filed: Mar. 12, 1990

[51] Int. Cl.$^5$ .................. H01N 55/00; C07F 5/02
[52] U.S. Cl. ........................ 514/64; 548/110
[58] Field of Search .................. 548/110; 514/64

[56] References Cited

U.S. PATENT DOCUMENTS

| | | | |
|---|---|---|---|
| 3,062,708 | 11/1962 | Updegraff | 167/30 |
| 3,211,679 | 10/1965 | Updegraff | 260/19 |
| 3,268,401 | 8/1966 | Birmbaum et al. | 167/38 |
| 3,686,398 | 8/1972 | Kohn et al. | 424/185 |
| 3,696,103 | 10/1972 | Cometti | 260/268 |
| 4,613,373 | 9/1986 | Umeno | 106/183 |

FOREIGN PATENT DOCUMENTS 62-277307 5/1986 Japan .

OTHER PUBLICATIONS

Wababayashi et al., Chemical Abstracts, vol. 111 (1989), 214696r.
Derwent Abstract 5188957 (6–1989).
Compte Rendus Hebdomadaires des Seances de l'Academie des Sciences, p. 319, vol. 254 (1962).

*Primary Examiner*—Richard L. Raymond
*Attorney, Agent, or Firm*—R. C. Gaffney; L. S. Squires

[57] ABSTRACT

Organoborane triazoles compounds having the formula:

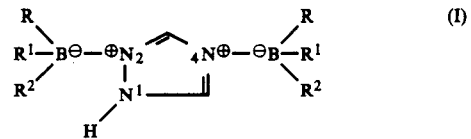

wherein R, $R^1$ and $R^2$ are defined in the description, and intermediates therefor are disclosed.

The compounds of formula I are especially useful as agricultural fungicides.

19 Claims, No Drawings

FUNGICIDAL TRIAZOLE BIS(TRIPHENYLBORANES), DERIVATIVES THEREOF AND USE THEREOF

BACKGROUND OF THE INVENTION

This invention relates to certain triazole bis-borane complexes and derivatives thereof. In a further aspect, the invention relates to the use of such complexes as fungicides and especially as agricultural fungicides.

A large amount of crop loss and plant damage is incurred each year due to plant diseases caused by four classes of fungi: Ascomycetes, causing a large number of leaf spots, blights, soil-bourn and post-harvest diseases; Deuteromycetes, also causing a large number of leaf spots, blights, soil-bourn and post-harvest diseases; Basidiomycetes, causing rust, smuts, bunts and soil borne-diseases; and Phycomycetes, causing downy mildews, leaf blights and soil-bourn diseases.

Leaf spot and blight diseases, such as those induced by species of Leptosphaeria, Mycosphaerella, Alternaria, and Helminthosporium cause damage to many crops such as maize, wheat, banana, and solanaceous crops and are difficult to control.

Various species of the genus Botrytis are responsible for diseases causing large losses in numerous vegetable, ornamental and vine crops. Present fungicides such as benzimidazoles and dicarboximides cannot adequately control these diseases due to the development of resistance by the pathogen.

The late blights and downy mildew plant diseases produced, for example, by Phytophthora and Plasmopara are very destructive to grape and solanaceous crops, e.g., potato, tomato. These diseases are also difficult to control due to the development of resistance to the leading systemic fungicides used to control these diseases.

Thus, it would be desirable to develop new fungicides which are effective to control plant diseases and especially in the case of late blights, mildew and Botrytis-produced diseases which are not subject to cross-resistance of the pathogen and which do not cause significant injury to the plants (i.e., are relatively non-phytotoxic).

U.S. Pat. No. 3,062,708 generally teaches that amine complexes of triphenylborane with certain Lewis bases have antifungal activity. The patent shows in vitro activity with respect to complexes of triphenylborane with imidazole, pyridine, and a number of other Lewis bases and illustrates in vivo activity against tomato early blight, bean rust, late blight and seed rot (*Pythium ultimum*) with respect to certain triphenylborane amines including complexes with piperidine, pyridine and 4-ethylpyridine.

U.S. Pat. No. 3,211,679 teaches that triarylborane amine complexes with pyridine or a variety of substituted pyridines are useful as toxicants for antifouling paint and that such paints import residual toxicity to marine borers to wood structures.

U.S. Pat. No. 3,268,401 teaches the use of certain complexes of triarylboranes with Lewis bases/including triphenylborane-piperadine; triphenyl-piperazine; triphenyl-pyridine; triphenyl-imidazole and others, as seed coatings to protect the seeds from soil borne microorganisms.

U.S. Pat. No. 3,686,398 teaches that certain 10,9-boroxarophenanthrenes are useful to control fungi and exhibited preventative control of bean rust and celery late blight.

U.S. Pat. No. 3,696,103 teaches that certain di(substituted and unsubstituted phenyl)azaborolidines exhibit fungicidal, insecticidal, acaricidal and herbicidal activity. The fungicidal activity is described as polyvalent and is shown against bean anthracnose (*Collectrotrichum lindemythianum*), tomato mildew (late blight) (*Phytophthora infestans*), tobacco mildew (blue mold) (*Peronospora tabaci*), cucumber (powdery) mildew (*Erysiphe cichoracearum*) and wheat rust (*Puccinia glumarum*) at quantities of between 10 and 200 g of active substance per hectoliter of liquid diluent such as water.

U.S. Pat. No. 4,613,373 teaches that certain tetra(substituted and unsubstituted phenyl) boranes complexed with a heterocyclic amine are useful as antifouling, antiseptic, and antifungal agents in many industrial applications. In vitro inhibiting activity of certain of patentees compounds against certain fungi are shown in Table 4 of the patent.

Based on the Derwent Abstract, Japanese Patent Application Publication No. 62-277307 describes complexes of tri(substituted phenyl)borane with amines and nitrogen containing heterocycles as useful as insecticides, miticides and nematocides. Based on Derwent Abstract No. 5188957, Japanese Patent Application publication JP No. 1056684 published Mar. 3, 1989 discloses certain tetraphenylboron-onium complexes useful as agricultural and industrial fungicides.

SUMMARY OF THE INVENTION

The present invention provides compounds having fungicidal activity against certain plant diseases and which are either nonphytotoxic or exhibit acceptable levels of phytotoxicity with respect to a number of crops. Certain of the compounds exhibit protective or preventative activity against a broad spectrum of Botrytis diseases, mildews, blights and leafspot and leaf blights induced by Septoria, and are not affected by cross-resistance of the pathogen to other fungicides. Although primarily effective as preventative fungicides certain of the compounds may also be effective as eradicants with respect to certain fungal diseases.

The present invention provides triazole bis(organoborane) complexes having the formula (I) hereinbelow:

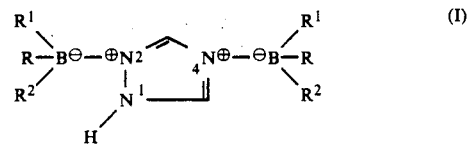

wherein:

R, $R^1$ and $R^2$ are independently selected from the group of phenyl and substituted phenyl having one or two substituents independently selected from the group of fluoro, chloro, bromo and trifluoromethyl.

In a further aspect, the invention provides a fungicidal composition comprising a compatible carrier and a fungicidally effective amount of the compound(s) of the invention or mixtures thereof.

The invention also provides a method for preventing or controlling fungi, which comprises applying an amount of a compound of Formula I or mixtures thereof to such fungi or its habitat which is effective to prevent or inhibit or arrest the growth of the fungi.

In another aspect the invention provides a method for preventing or controlling fungal plant diseases which comprises applying to the plant an amount of the compound(s) of Formula I or mixtures thereof which is effective to prevent or inhibit the growth of the fungal pathogen producing the disease.

The present invention also provides chemical intermediates, and processes for preparing the compounds of Formula I.

The invention will be further described hereinbelow.

FURTHER DESCRIPTION OF THE INVENTION AND THE PREFERRED EMBODIMENTS

Illustrations of typical compounds of Formula I can be had by reference to Examples 1-3 set forth hereinbelow on Pages 20-24.

Generally, in terms of fungicidal effectiveness and spectrum of activity, and/or ease of manufacture the preferred compounds are those wherein R, $R^1$ and $R^2$ are independently phenyl or substituted phenyl having a single substituent selected from the group of fluoro and chloro.

Especially preferred in terms of the magnitude of antifungal activity or spectrum of antifungal activity, and/or crop safety are those compounds wherein R, $R^1$ and $R^2$ are independently phenyl or fluorophenyl especially 4-fluorophenyl.

The compounds, 1,2,4-triazole-bis(triphenylborane) and 1,2,4-triazole-bis[tri(4-fluorophenyl)borane] exhibit especially good preventative fungicidal activity.

In terms of manufacturing ease, the compounds wherein R, $R^1$ and $R^2$ are the same are preferred, i.e., (IA)

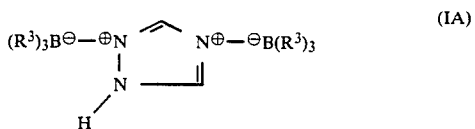

(IA)

wherein $R^3$ is as defined for R hereinabove.

DEFINITIONS

As used herein the following terms have the following meanings unless expressly stated to the contrary:

The term "alkyl" refers to both straight- and branched-chain alkyl groups The term "lower alkyl" refers to alkyl groups having a total of from 1 through 6 carbon atoms, preferably 1 through 4 carbon atoms and includes primary, secondary and tertiary alkyl groups. Typical lower alkyls include, for example, methyl, ethyl, n-propyl, isopropyl, n-butyl, t-butyl, pentyl, hexyl and the like.

The term "lower alkoxy" refers to the group —OR, wherein R, is lower alkyl.

The term "halo" refers to the group of fluoro, chloro, bromo and iodo unless expressly defined as referring to a more limited group, e.g. fluoro, chloro and bromo.

The term "aralkyl" refers to the group

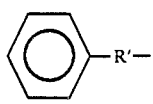

wherein R' is lower alkyl having through 4 carbon atoms and preferably is methyl or ethyl.

The term "lower haloalkyl" refers to haloalkyl compounds having 1 through 4 carbon atoms and 1 through 3 halo atoms independently selected from the group of fluoro, chloro, bromo. Preferably the lower haloalkyl group has 1 or 2 carbon atoms.

The term "1,2,4-triazole bis(triphenylborane)" refers to the compound

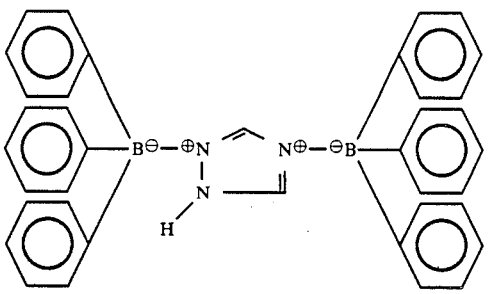

The term "room temperature" or "ambient temperature" refers to about 20°-25° C.

SYNTHESIS

The compounds of Formula I can be conveniently prepared by reacting the appropriately substituted or unsubstituted phenyl Grignard reagent with borontrifluoride etherate and reacting the resulting boron intermediate with 1,2,4-triazole, typically in situ to form the desired compound of Formula I

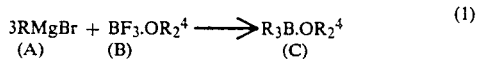

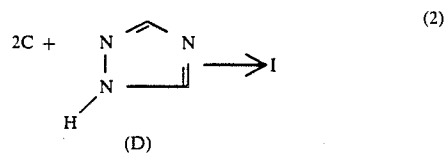

wherein R is as defined hereinabove and $R^4$ is lower alkyl, preferably ethyl.

Step 1 of this process is a Grignard reaction and typically is effected by contacting Grignard reagent (A) with the boron trifluoride etherate (B) under reactive conditions, preferably in an inert organic solvent under substantially anhydrous conditions. Typically, this step is conducted at temperatures in the range of about from 15° C. to 80° C, preferably 20° C. to 35° C., for about from 2 to 24 hours, preferably about from 2 to 4 hours, using about from 3 to 9, preferably 3 to 6 moles of Grignard reagent (A) per mole of Compound (B).

Suitable organic solvents which can be used include, for example, tetrahydrofuran, alkyl ethers (e.g., ethyl ether), hexane, and the like, and compatible mixtures thereof. Best results are generally obtained using tetrahydrofuran, ethyl ether or glyme as the solvent.

By using a mixture of Grignard reagents having different phenyl or substituted phenyl groups (i.e., RMgBr +$R^1$MgBr+$R^2$MgBr) or in some cases by conducting the reaction in stages using a different Grignard reagent in each stage, a product can be prepared having different phenyl substituents.

The second step can be effected by contacting intermediate C with the triazole (D) under reactive conditions, preferably in an inert organic solvent. Typically, this reaction is conducted in situ without isolation of intermediate C.

Typically, this reaction step is conducted at reaction temperatures in the range of about from 15° to 80° C., preferably about from 20° to 40° C. for about from 2 to 24 hours, using about from 0.4 to 1, preferably about ½ mole of compound D per mole of compound C.

Suitable inert organic solvents which can be used include, for example, the solvents treated previously with respect to the Grignard reaction. Since this reaction step is typically conducted in situ, the same solvent used in the first step will generally be used in this step.

The starting materials of Formula A are Grignard reagents and can be prepared via standard procedures such as, for example, described in P. E. Pearson, D. Cowan, J. D. Becker, J. Org. Chem. 24, 504 (1959). The triazole starting material of Formula D is, of course, a known compound and can be prepared according to known procedures such as those described in "Organic Synthesis," Volume 5, pages 1070–1074, 1973 (John Wiley & Sons, Inc.).

In the case where mixed phenyl products (i.e., R, $R^1$ and/or $R^2$ are the same or different) are prepared it is generally preferred to use the product as a mixture to avoid the costs involved in separating a given compound from the mixture. Where an individual compound having different R, $R^1$, and/or $R^2$ groups is desired, it is preferred to use the synthesis procedures described below.

The compounds of Formula I can also be prepared by the following schematically represented process:

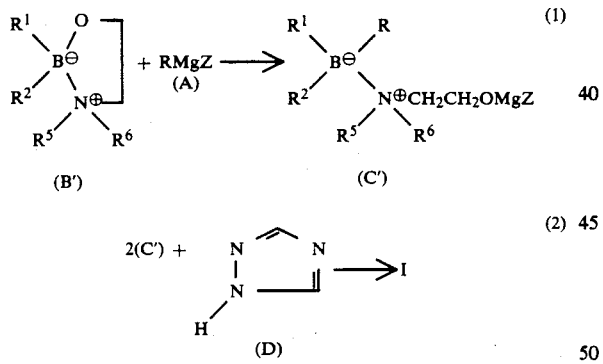

wherein R, $R^1$, and $R^2$ are as defined hereinabove, $R^5$ and $R^6$ are independently hydrogen or lower alkyl, preferably hydrogen or methyl, and Z is chloride, bromide or iodide.

Step 1 of this process is a Grignard reaction and typically is effected by contacting Compound (B) with the Gri9nard reagent (A) under reactive conditions, preferably in an inert organic solvent under substantially anhydrous conditions. Typically, this step is conducted at temperatures in the range of about 15° C. to 80° C., preferably 20° C. to 35° C., for about from 2 to 24 hours, preferably about from 2 to 4 hours, using about from 1 to 3.5, preferably 1 to 3 moles of Grignard reagent (A) per mole of Compound (B').

Suitable organic solvents which can be used include, for example, tetrahydrofuran, alkyl ethers (e.g. ethyl ether), hexane, and the like, and compatible mixtures thereof. Best results are generally obtained using tetrahydrofuran, ethyl ether or glyme as the solvent.

The second step can be effected by contacting intermediate (C') with the appropriately substituted or unsubstituted triazole (D), preferably in an inert organic solvent, under reactive conditions. The second step can be conveniently conducted in situ without separation of intermediate II.

Typically, this step is conducted at temperatures in the range of about from 20° C. to 35° C., preferably 20° C. to 25° C., for about from 2 to 24 hours, preferably 10 to 24 hours, using about from 1 to 2.5, preferably about 2 mol, of Compound (C') per mol of triazole (D). Typically, about from 1 to 3 moles of base are used per mole of triazole (D).

Suitable inert organic solvents which can be used include, for example, the solvents listed above with respect to step 1, and compatible mixtures thereof. Since most conveniently, the second step is conducted in situ, the same solvent will generally be used in the second step as used in the first step.

The preparation of starting materials (B') is, for example, described in Y. Rasiel and H. K. Zimmerman, Ann. 649, 111 (1961) or by R. L. Lestinger and I. Skoog, J. Am. Chem. Soc. 77, 2491 (1955), and in the case where $R^1$ and $R^2$ are phenyl and $R^5$ and $R^6$ are hydrogen, is a commercially available material. The starting materials of Formula (B') can also be prepared by hydrolysis and oxidation of the corresponding optionally substituted triphenylborane alkali metal hydroxide adduct by procedure of P. Denisevich illustrated hereinbelow in Preparation A. In the case where $R^1$ and $R^2$ are different the procedure described in D. Giraud et al, *Compte Rendus Hebdomadaires des Sceances de l'Academie des Sciences*, p. 319 v. 254 (1962) can be applied to prepare the borane intermediates (C') for the compounds of Formula I.

The compounds of Formula I also generally can be conveniently prepared via the process of P. Kenny using an exchange reaction of an triazole with a $(RR^1R^2)$ boron-ammonia complex:

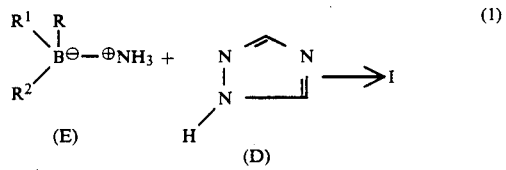

wherein R, $R^1$ and $R^2$ are defined hereinabove.

In accordance with this process, Compound (E) is contacted with Compound (D) under reactive conditions, preferably in a inert organic solvent under substantially anhydrous conditions.

Preferably, this process is conducted at temperatures in the range of about from 0° C. to reflux, conveniently about 20° C. to 25° C. for about 1 to 72 hours, using about from 1 to 0.5 moles of Compound (D) per mole of Compound (E). Suitable inert organic solvents which can be used include, for example, halogenated alkanes, for example, chloroform, methylene chloride; lower alkenols, for example, methanol, ethanol; acetone and the like and compatible mixtures thereof. The starting material of Formula (E) can be prepared by known procedures such as, for example, described by D. Giraud et al, *Compte Rendus Hebdomadaires des Sceances de l'Academie des Sciences*, p. 319, v. 254 (1962), or by obvious modifications thereof (e.g., use of appropriately substituted reactants and appropriate solvents). Compound (E) can also be conveniently prepared via the reaction of intermediate C' with ammonia.

The unsubstituted phenyl compound of Formula I, i.e., 1,2,4-triazole-2,4-bis(triphenylborane) can also be prepared via the reaction of triphenylboron with 1,2,4-triazole. This reaction is preferably conducted in an inert organic solvent, for example, liquid halogenated alkanes, e.g., methylene chloride, chloroform and the like. The reaction is typically conducted at temperatures in the range of about from 20° to 40° C., preferably 20° to 25° C. for about 3 to 10 hours using about 2 to 3 moles of triphenylboron per mole of triazole.

GENERAL PROCESS CONDITIONS

In the above-described processes, the products can be recovered from the respective reaction product mixtures by any suitable separation and purification procedure, such as, for example, extraction, trituration, and recrystallization.

Suitable separation and purification procedures are, for example, illustrated in the examples set forth hereinbelow.

Generally, the reactions described above are conducted as liquid phase reactions and hence pressure is generally not significant except as it affects temperature (boiling point) where reactions are conducted at reflux. Therefore, these reactions are generally conducted at pressures of about from 300 to 3,000 mm of mercury and conveniently are conducted at about atmospheric or ambient pressure.

It should also be appreciated that where typical or preferred process conditions (e.g., reaction temperatures, times, mole ratios of reactants, solvents, pressures, etc.) have been given, that other process conditions could also be used unless otherwise stated. Optimum reaction conditions (e.g., temperature, reaction time, mole ratios, solvents, etc.) may vary with the particular reagents or organic solvents, used but can be determined by routine optimization procedures.

UTILITY

The compounds of the present invention are effective in controlling fungal plant diseases, including downy mildew, leaf blights, leaf spots, damping-off diseases, Botrytis diseases, and post-harvest diseases. Certain of the compounds further exhibit a broad spectrum of activity whereas as others are more specific for particular fungal diseases. The particular spectrum of activity for a given compound can be determined by routine testing such as described in Example 5 hereinbelow. The compounds are generally more effective as preventative fungicides than eradicant fungicides. A number of the compounds are especially effective in preventing certain species of Botrytis diseases, mildews, late blights in solanaceous crops, and/or Septoria leaf spot diseases.

The compounds are applied to the subject plants in fungicidally effective amounts. When applied as preventative fungicides, the compounds are preferably applied at pre-scheduled times prior to the detection of plant infection or immediately upon the detection of infection. The optimum fungicidally effective amount will, of course, depend on several factors such as the host, the type of fungus, weather conditions, and the particular compound of the invention. Generally, however, the compounds are preferably applied at a rate of about from 0.2 to 2.5 kg per hectare for preventative application, and 1 to 3 kg per hectare for eradicant application. The compounds may also be applied for seed treatments. Generally, the compounds are applied as seed treatments at a rate of about 0.5 to 32 g per 100 kg of seeds. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable solutions, as emulsifiable concentrates, as solutions, or as any of several other known types of formulations, depending on the desired mode of application.

Wettable powders are in the form of finely divided particles which disperse readily in water or other dispersant. These compositions normally contain from about 5% to 80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols, and polyvinyl alcohols; polyethylene oxides, sulfonated animal and vegetable oils; sulfonated petroleum oils, fatty acid esters of polyhydric alcohols and the ethylene oxide addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively course particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art. The percentages by weight of the fungicide may vary according to the manner in which the composition is to be applied and the particular type of formulation, but in general comprise 0.05% to 95% of the toxicant by weight of the fungicidal composition, and depending on whether the composition is intended for direct application or dilution prior to application. The compounds are typically applied at rates in the range of about from 0.1 to 5 kg/hectare, preferably 0.2 to 3 kg/hectare, and typically are applied as foliage sprays.

The fungicidal compositions may be formulated and/or applied with other ingredients, including wetting agents, emulsifiers, adjuvants, stabilizers, etc., as well as other compatible active ingredients such as other fungicides, insecticides, nematocides, bactericides, plant growth regulators, fertilizers, etc.

A further understanding of the invention can be had in the following non-limiting Preparation(s) and Example(s). Wherein, unless expressly stated to the contrary, all temperatures and temperature ranges refer to the Centigrade system and the term "ambient" or "room temperature" refers to about 20°–25° C. The term "percent" or "%" refers to weight percent and the term "mol", "mole" or "moles" refers to gram moles. The term "equivalent" refers to a quantity of reagent equal in mole equivalents to the mole equivalent of the preceding or succeeding reactant recited in that example or preparation in terms of finite moles or finite weight or volume.

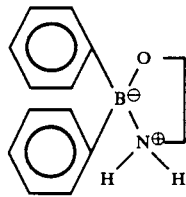

This preparation illustrates the preparation of the title compound via the method of P. Denisevich, Jr.

Aqueous 10 wt% hydrochloric acid is slowly added to 250 g of a solution containing 22.5 g of triphenylborane.sodium hydroxide. The addition of hydrochloric acid is continued until a pH of 1.2. During the addition, cooling is provided to maintain the temperature of the reaction mixture below 30° C. Eighty (80) ml of ethyl ether is added and the mixture stirred overnight (about 10–12 hours) at room temperature during which time a slow steady stream of air is passed through the mixture. Fifty (50) ml of ethyl ether is added to compensate for evaporation losses. The reaction mixture forms a two-phase system. The ethyl ether phase is separated, washed with water and then added to 4.9 g of 2-aminoethanol. The mixture is stirred for one hour at room temperature and then filtered. The recovered solids are 8 washed with water, affording 14 4 g of the title compound m.p. 186°–188° C.

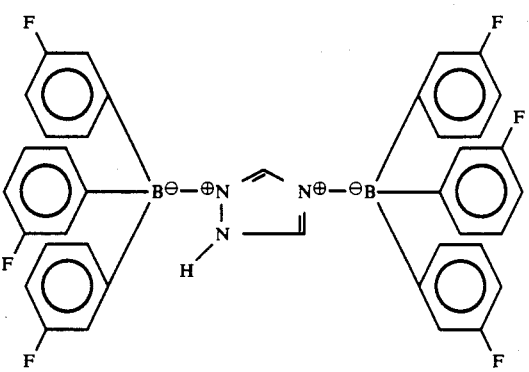

In the example, 0.065 mole of 3-fluorophenyl magnesium bromide in 10 ml of diethyl ether is added dropwise to 0.021 mole of borontrifluoride ethyl etherate [i.e., $BF_3.O(C_2H_5)_2$] in 20 ml of diethyl ether at room temperature. The resulting mixture is stirred overnight, about 14–16 hours, at room temperature and then heated for two hours at 40° C. 0.021 Mole of 1,2,4-triazole is then added and the mixture stirred for three hours. One hundred (100) ml of aqueous 10 wt. % hydrochloric acid is then slowly added to quench the reaction. The product mixture is extracted twice with 200 ml of ethyl ether. The combined extract is washed with water, then with an aqueous sodium chloride solution. The ethyl ether layer is then removed, dried over magnesium sulfate, and evaporated to dryness affording the title compound as a yellow solid m.p. 196°–198° C.

Similarly, by applying the above procedure using the appropriate starting materials the following compounds can be prepared.

1,2,4-triazole-2,4-bis[tri(2-chlorophenyl)borane];
1,2,4-triazole-2,4-bis[tri(3-bromophenyl)borane];
1,2,4-triazole-2,4-bis[tri(4-trifluoromethylphenyl)borane];
1,2,4-triazole-2,4-bis[tri(3-chlorophenyl)borane];
1,2,4-triazole-2,4-bis[tri(4-bromophenyl)borane];
1,2,4-triazole-2,4-bis[tri(3-trifluoromethylphenyl)borane];
1,2,4-triazole-2,4-bis[tri(2-fluorophenyl)borane];
1,2,4-triazole-2,4-bis[tri(2-chloro-4-trifluoromethylphenyl)borane];
1,2,4-triazole-2,4-bis[tri(3,4-dichlorophenyl)borane];
1,2,4-triazole-2,4-bis[tri(2-bromo-4-fluorophenyl)borane];
1,2,4-triazole-2,4-bis[tri(3,5-dibromophenyl)borane];
1,2,4-triazole-2,4-bis[tri(2,6-dichlorophenyl)borane];
1,2,4-triazole-2,4-bis[tri(2,4-trifluoromethylphenyl)borane];
1,2,4-triazole-2,4-bis[tri(2-fluoro-4-trifluoromethylphenyl) borane]; and 1,2,4-triazole-2,4-bis[tri(4-bromo-2-trifluoromethylphenyl)borane].

Similarly, by following the same procedure using the appropriate mixture of Grignard reagents, the following compounds can be prepared:

1,2,4-triazole-2,4-bis[(4-bromophenyl)-di(2-chlorophenyl)-borane];
1,2,4-triazole-2,4-bis[(3-chlorophenyl)-di(4-fluorophenyl)-borane];
1,2,4-triazole-2,4-bis[(2-fluorophenyl)-di(3-trifluoromethyl-phenyl)borane];
1,2,4-triazole-2,4-bis[(3-fluorophenyl)-di(4-trifluoromethyl-phenyl)borane];

1,2,4-triazole-2,4-bis[(2-bromophenyl)-di(2,4-dichlorophenyl)-borane];

1,2,4-triazole-2,4-bis[(4-chlorophenyl)-di(2-fluoro-4-tri-fluoromethylphenyl)borane];

1,2,4-triazole-2,4-bis[(3-bromophenyl)-di(3,4-dichlorophenyl)-borane;

1,2,4-triazole-2,4-bis[(3,5-dibromophenyl)-di(2,4-tri-fluoromethylphenyl)borane];

1,2,4-triazole-2,4-bis[(3-bromophenyl)(4-chlorophenyl)(2-fluorophenyl)borane]

1,2,4-triazole-2,4-bis[(2-chlorophenyl)(3-trifluoromethyphenyl)(4-trifluoromethylphenyl)borane];

1,2,4-triazole-2,4-bis[(3-bromophenyl)(4-fluorophenyl)-(2-chloro-4-trifluoromethylphenyl)borane];

1,2,4-triazole-2,4-bis[(4-bromo-2-trifluoromethylphenyl)-(4-chlorophenyl)(2,4-difluorophenyl)borane];

1,2,4-triazole-2,4-bis[(2-chloro-3-fluorophenyl)-(3,4-dichlorophenyl)(2,6-di-fluorophenyl)borane]; and 1,2,4-triazole-2,4-bis[(3,5-dichlorophenyl)(3-fluoro-4bromophenyl)(2-fluoro-4-trifluoromethylphenyl)borane].

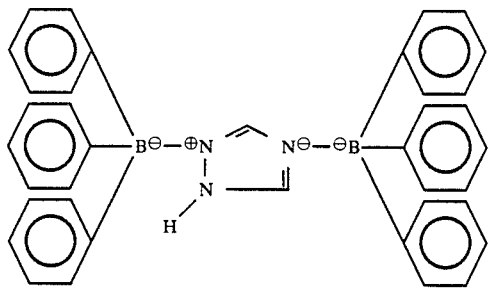

The title compound can be prepared by adding 0.04 mole of 1,2,4-triazole to 0.08 mole of triphenylborane in 20 ml of diethylether at room temperature under nitrogen. The mixture is stirred under the inert atmosphere (i.e., nitrogen) for six hours at room temperature. The title compound is collected as a precipitate, m.p. 94°–96° C.

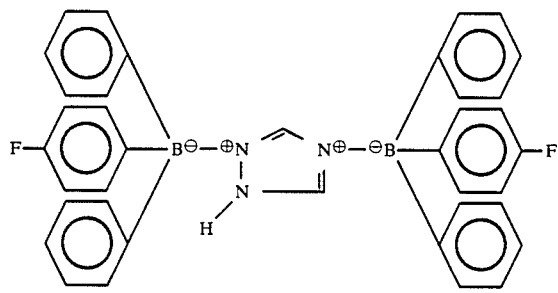

The title compound can be prepared by adding 0.04 mole of 4-fluorophenyl magnesium bromide to a stirred mixture containing 0.013 mole of 2-amino diphenylborinate in 40 ml of diethyl ether at room temperature. The mixture is stirred three hours and then 0.0065 mole of 1,2,4-triazole in 10 ml of diethyl ether is added followed by stirring overnight (about 14–16 hours) at room temperature. The title compound can be isolated by dilution with 100 ml of aqueous 5 wt% hydrochloric acid, extraction with diethyl ether and evaporation of the etherial extracts.

Similarly by applying the same procedure using the corresponding starting materials the compounds listed in Example 1 can also be prepared by this procedure.

EXAMPLE 4

Similarly, by applying the same general procedures described in Examples 1 and 2 using the appropriate starting materials, the compounds identified in Table A below were prepared:

TABLE A $$(R)_3B^{\ominus}-^{\oplus}N \overset{\frown}{\underset{\underset{H}{N}}{|}} N^{\oplus}-^{\ominus}B(R)_3 \qquad (IA)$$

| No. | R | Melting Point °C. |
|-----|---|-------------------|
| 1 | phenyl | 94–96 |
| 2 | 3-fluorophenyl | 196–198 |
| 3 | 4-fluorophenyl | 181–182 |
| 4 | 4-chlorophenyl | 179–181 |

EXAMPLE 5

The compounds identified in Table A hereinabove were tested for the preventative control of certain plant diseases by the procedures described below. The results of this testing is set forth in Table 1 hereinbelow, wherein Compound Numbers refer to the Compound Numbers assigned the respective compounds in Table A.

Tomato Late Blight (TLB)

Compounds of the invention were tested for the preventative control of the Tomato Late Blight organism *Phytophthora infestans*. Three to six week old tomato (cultivar Bonny Best) seedlings were used. The tomato plants were sprayed with either a 500 or 200 ppm suspension of the test compound in acetone, water and a non-ionic emulsifier. The sprayed plants were then inoculated one day later with the organism, placed in an environmental chamber and incubated at 66° F. to 68° F. and 100% relative humidity for 16 to 24 hours.

Following the incubation, the plants were maintained in a greenhouse for approximately 7 days. The percent disease control provided by a given test compound was based on the percent disease reduction relative to untreated check plants.

The averaged results are reported in Table 1.

Rice Blast (RB)

Compounds of this invention were tested for control of the Rice Blast organism *Piricularia oryzae*, using 10 to 14 day old rice plant seedlings (Calrose M-9 variety). Seedling plants were sprayed with a 500 or 200 ppm solution of the test compound in acetone, water and a non-ionic emulsifier. The sprayed plants were inoculated 1 day later with the organism in an environmental chamber. After inoculation, the plants were kept in an environmental chamber for about 48 hours under conditions of about 72° F. to 75° F. and about 100% relative humidity. Following the incubation period, the plants were placed in a greenhouse with a temperature of about 80° F. and maintained with bottom watering for about 12 to 16 days. The percent disease control provided by a given test compound is based on a comparison of the percentage disease relative to the percent disease development on untreated check plants. The averaged results are reported in Table 1.

Celery Late Blight (CLB)

The Celery Late Blight tests were conducted using celery (Utah) plants 11 weeks old. The Celery Late Blight organism was *Septoria apii*. The celery plants were sprayed with either 500 or 200 ppm solutions of the test compound mixed with acetone, water and a nonionic emulsifier. The plants were then inoculated one day later with the organism and placed in an environmental chamber and incubated at 66° F. to 68° F. in 100% relative humidity for approximately 48 hours. Following the incubation, the plants were allowed to dry and then were maintained in a greenhouse for approximately 14 days. One plant was used per compound Six untreated plants were used as the check for each screening group of compound. The percent disease control provided by a given candidate toxicant is based on the percent disease reduction relative to untreated check plants. The results are reported in Table 1.

Bean Powdery Mildew (BPM)

The compounds of the invention were tested for the control of the Bean Powdery Mildew organism, *Erysiphe polygoni*. Seedling bean plants were sprayed with a 500 or 200 ppm solution of the test compound in acetone, water and a nonionic emulsifier. The sprayed plants were then inoculated 1 day later with the organism The plants were maintained for 10 days at temperatures of 68° F. at night with daytime temperatures of 72° F. to 80° F.; relative humidity was maintained at 40% to 60%. One plant was used per compound Six untreated plants were used as the check for each screening group of compounds. The percent disease control provided by a given test compound was based on the percent disease reduction relative to the untreated check plants The results are reported in Table 1.

Bean Rust (BR)

The Leaf Rust test was made using pinto beans. The pathogen was *Uromyces phaseoli tipica*. The bean plants were sprayed with either a 500 or 200 ppm solution of the test compound in an acetone-water mixture containing a nonionic emulsifier. The treated plants were inoculated thereafter with the pathogen and then incubated in an environmental chamber for approximatley 20 hours at 100% relative humidity and a temperature of 68° F. to 70° F. The plants were then removed from the chamber, allowed to dry, and then maintained in a greenhouse at a 60% to 80% relative humidity. The amount of infection on the leaves was rated after about 14 days. The percent disease control provided by a given test compound was based on the percent disease reduction relative to untreated check plants. The results are reported in Table 1.

TABLE 1

Preventative Fungicidal Activity
(Dosage rate 200 ppm unless otherwise indicated)

| Compound NO. | TLB | RB | CLB | BPM | BR | BB |
|---|---|---|---|---|---|---|
| 1 | 78 | 86 | 100 | 100 | 0 | NA |
| 2 | 65 | 73 | 0 | 100 | 90 | 0 |
| 3 | 87 | 0 | 100 | 0 | 100 | 100 |
| 4 | 100 | 0 | 0 | 0 | 0 | 100 |

TLB = Tomato Late Blight
RB = Riceblast
CLB = Celery Late Blight
BPM = Bean Powdery Mildew
BR = Bean Rust
BB = Bean Botrytis
NA = Test results not available Obviously, many modifications and variations in the invention, described hereinabove and below, can be made without departing from the essence and scope thereof.

What is claimed is:

1. A compound having the formula:

$$R_2^{R}\!\!>\!\!B^{\ominus}\!\!-\!\!{}^{\oplus}N_2 \diagup\!\!\diagdown {}_4N^{\oplus}\!\!-\!\!{}^{\ominus}B\!\!<\!\!{}_{R^2}^{R^1} \quad (I)$$
$$\underset{H}{\overset{|}{N^1}}\!\!\!\text{———}$$

wherein:
R, RT¹, and R² are independently selected from the group of phenyl and substituted phenyl having 1 or 2 substituents independently selected from the group of fluoro, chloro, bromo and trifluoromethyl.

2. The compound of claim 1 wherein R, R¹, and R² are independently selected from the group of phenyl and mono-substituted phenyl having its single substituent selected from the group of fluoro and chloro.

3. The compound of claim 1 wherein said compound has the formula $$(R^3)_3B^{\ominus}\!\!-\!\!{}^{\oplus}N \diagup\!\!\diagdown N^{\oplus}\!\!-\!\!{}^{\ominus}B(R^3)_3$$
$$\underset{H}{\overset{|}{N}}\!\!\!\text{———}$$

wherein R³ is as defined for R in claim 1.

4. The compound of claim 3 wherein R³ is selected from the group of phenyl and monosubstituted phenyl having its substituent selected from the group of fluoro, chloro, bromo and trifluoromethyl.

5. The compound of claim 3 wherein R³ is selected from the group of phenyl, 3-fluorophenyl, 4-fluorophenyl, 2-fluorophenyl, 2-chlorophenyl, 3-chlorophenyl, and 4-chlorophenyl.

6. The compound of claim 3 wherein R³ is phenyl

7. The compound of claim 3 wherein R³ is 4-fluorophenyl.

8. The compound of claim 3 wherein R³ is trifluoromethylphenyl.

9. The compound of claim 8 wherein R³ is 4-trifluoromethylphenyl.

10. The compound of claim 3 wherein R³ is bromophenyl.

11. The compound of claim 10 wherein R³ is 4-bromophenyl.

12. A method for controlling fungi which comprises contacting said fungi or its habitats with a fungicidally effective amount of a compound according to claim 1.

13. A method for controlling fungi which comprises contacting said fungi or its habitats with a fungicidally effective amount of a compound according to claim 3.

14. A method for controlling fungi which comprises contacting said fungi or its habitats with a fungicidally effective amount of a compound according to claim 6.

15. A method for controlling fungi which comprises contracting said fungi or its habitats with a fungicidally effective amount of a compound according to claim 7.

16. A fungicidal composition comprising a fungicidally effective amount of the compound claim 1 and a compatible carrier.

17. A fungicidal composition comprising a fungicidally effective amount of the compound claim 3 and a compatible carrier.

18. A fungicidal composition comprising a fungicidally effective amount of the compound claim 6 and a compatible carrier.

19. A fungicidal composition comprising a fungicidally effective amount of the compound claim 7 and a compatible carrier.

* * * * *

UNITED STATES PATENT AND TRADEMARK OFFICE
CERTIFICATE OF CORRECTION

PATENT NO. : 4,983,590
DATED : January 8, 1991
INVENTOR(S) : Tsze H. Tsang and Jon L. Strutzel It is certified that error appears in the above-identified patent and that said Letters Patent is hereby corrected as shown below:

Column 9, line 38, (omitted) should read --PREPARATIONS AND EXAMPLES--.
Column 9, line 38, (omitted) should read --PREPARATION A--.
Column 9, line 38, (omitted) should read --2-Aminoethyl Diphenyborinate--.
Column 9, line 67, "8 washed" should read --washed--.
Column 9, line 67, "14 4" should read --14.4--.
Column 10, line 1, (omitted) should read --EXAMPLE 1--.
Column 10, line 1, (omitted) should read --1,2,4-Triazole-2,4-bis-[tri(3-fluorophenyl)borane]--.
Column 11, line 21, "-4bromophenyl" should read ---4-bromophenyl--.
Column 11, line 23, (omitted) should read --EXAMPLE 2--.
Column 11, line 23, (omitted) should read --1,2,4-Triazole-2,4-bis-(triphenylborane)--.
Column 11, line 44, (omitted) should read --EXAMPLE 3--.
Column 11, line 44, (omitted) should read --1,2,4-Triazole-Bis(Diphenyl-4'-Fluorophenylborane)--.

UNITED STATES PATENT AND TRADEMARK OFFICE
CERTIFICATE OF CORRECTION

PATENT NO. : 4,983,590

DATED : January 8, 1991

INVENTOR(S) : Tsze H. Tsang and Jon L. Strutzel

It is certified that error appears in the above-identified patent and that said Letters Patent is hereby corrected as shown below:

Column 14, line 29 "$RT^1$" should read --$R^1$--.

Signed and Sealed this

Third Day of November, 1992

Attest:

DOUGLAS B. COMER

Attesting Officer

Acting Commissioner of Patents and Trademarks